(12) United States Patent
Archer et al.

(10) Patent No.: US 9,296,771 B2
(45) Date of Patent: Mar. 29, 2016

(54) LARGE SCALE PREPARATION METHOD FOR FUNCTIONALIZING THE SURFACE OF MAGNETIC MICROPARTICLES WITH AN INORGANIC PHOSPHOROUS DENDRIMER

(71) Applicants: Marie J. Archer, Berwyn Heights, MD (US); Baochuan Lin, Bethesda, MD (US)

(72) Inventors: Marie J. Archer, Berwyn Heights, MD (US); Baochuan Lin, Bethesda, MD (US)

(73) Assignee: The United States of America, as represented by the Secretary of the Navy, Washington, DC (US)

(*) Notice: Subject to any disclaimer, the term of this patent is extended or adjusted under 35 U.S.C. 154(b) by 29 days.

(21) Appl. No.: 14/208,265

(22) Filed: Mar. 13, 2014

(65) Prior Publication Data
US 2014/0275628 A1    Sep. 18, 2014

Related U.S. Application Data

(60) Provisional application No. 61/787,047, filed on Mar. 15, 2013.

(51) Int. Cl.
C40B 50/12    (2006.01)
A61K 8/24     (2006.01)
C07F 9/6593   (2006.01)

(52) U.S. Cl.
CPC .................................. *C07F 9/65815* (2013.01)

(58) Field of Classification Search
CPC .................... B01J 2219/00655; A61K 8/24
USPC ............................... 435/22; 560/17; 506/17
See application file for complete search history.

(56) References Cited

U.S. PATENT DOCUMENTS

| 4,454,234 | A | 6/1984 | Czerlinski |
| 5,091,206 | A | 2/1992 | Wang et al. |
| 5,648,124 | A | 7/1997 | Sutor |
| 5,834,121 | A | 11/1998 | Sucholeiki |
| 6,120,856 | A | 9/2000 | Liberti et al. |
| 6,548,264 | B1 | 4/2003 | Tan et al. |
| 6,656,587 | B2 | 12/2003 | Johnson et al. |

(Continued)

OTHER PUBLICATIONS

Archer et al., "Magnetic bead-based solid phase for selective extraction of genomic DNA," Anal. Biochem. 355, 285-297 (2006).

(Continued)

*Primary Examiner* — Kamal Saeed
*Assistant Examiner* — Janet L Coppins
(74) *Attorney, Agent, or Firm* — US Naval Research Laboratory; Rebecca L. Forman

(57) ABSTRACT

A method of attaching a phosphorous dendrimer onto magnetic microparticles by taking magnetic microparticles in a water-based solution, then performing a solvent exchange, then suspending the microparticles in a phosphorous dendrimer solution and shaking, then washing the microparticles with an organic solvent, and then washing the microparticles with a transition solvent. The solvent exchange is done by washing the microparticles with a first concentration of a transition solvent, then washing the microparticles with a second concentration of the transition solvent where the second concentration is greater than the first concentration, then washing the microparticles with an organic solvent, then washing the microparticles with the transition solvent, then washing the microparticles with the organic solvent, and then suspending the microparticles in the transition solvent. Also disclosed is the related phosphorous dendrimer made by this method.

20 Claims, 2 Drawing Sheets

(56) References Cited

U.S. PATENT DOCUMENTS

| | | |
|---|---|---|
| 6,773,812 B2 | 8/2004 | Chandler et al. |
| 6,964,747 B2 | 11/2005 | Banerjee et al. |
| 7,186,398 B2 | 3/2007 | Andres et al. |
| 7,214,427 B2 | 5/2007 | Huang et al. |
| 2004/0132044 A1 | 7/2004 | Ritterband |
| 2005/0009002 A1 | 1/2005 | Chen et al. |
| 2008/0293594 A1* | 11/2008 | Archer et al. ............ 506/17 |

OTHER PUBLICATIONS

Archer et al., "Development and Characterization of a Solid Phase for Single-Step Enrichment of Pathogenic Targets," The Open Analytical Chemistry Journal, 2, 47-54 (2008).

Horak et al., "Preparation and properties of magnetic nano- and microsized particles for biological and environmental separations," J. Sep. Sci., 30, 1751-1772 (2007).

Launay et al., "A General Synthetic Strategy for Neutral Phosphorus-Containing Dendrimers," Angew. Chem. Int. Ed. Engl., 33, 1589-1592 (1994).

Rana et al., "Synthesis of magnetic beads for solid phase synthesis and reaction scavenging," Tetrahedron Letters, 40, 8137-8140 (1999).

Pan et al., "Dendrimer modified magnetite nanoparticles for protein immobilization," Journal of Colloid and Interface Science, 284, 1-6 (2005).

Turrin et al., "Surface, core, and structure modifications of phosphorus-containing dendrimers. Influence on the thermal stability," Tetrahedron, 59, 3965-3973 (2003).

* cited by examiner

| (a) (PRIOR ART) | (b) (PRESENT INVENTION) |
| --- | --- |
| 500 μg beads (2 μm diameter) | 10 mg beads (1 μm diameter) |
| Wash with water (1 ml) x 5 | Wash with water (200 μl) x 1 |
| ↓ | ↓ |
| Re-suspend in 1 ml of ethanol | Wash with 50% ethanol (400 μl) x 2 |
| ↓ 8 hr shaking-90 rpm | ↓ |
| Re-suspend in 1 ml of dichloromethane | Wash with 100% ethanol (400 μl) x 2 |
| ↓ 18 hr shaking-90 rpm | ↓ |
| Transfer beads to fresh tubes | Wash with dichloromethane (1 ml) x 3 |
| ↓ | ↓ |
| Re-suspend in 1 ml of dendrimer solution at 1% (w/v) | Wash with 100% ethanol (1 ml) x 1 |
| ↓ 12 hr shaking-90 rpm | ↓ |
| Wash with dichloromethane (1 ml) x 3 | Wash with dichloromethane (1 ml) x 1 |
| ↓ | ↓ |
| Wash with 95% ethanol (1 ml) x 3 | Re-suspend in 100% ethanol (1 ml) |
| ↓ | ↓ |
| Wash with 100% ethanol (1 ml) x 3 | Transfer to fresh tubes |
|  | ↓ |
|  | Re-suspend in 1.5 ml of dendrimer solution at 2% (w/v) |
|  | ↓ 22 hr shaking-90 rpm |
|  | Wash with dichloromethane (1 ml) x 5 |
|  | ↓ |
|  | Wash with 100% ethanol (1 ml) x 4 |

FIG. 1

LARGE SCALE PREPARATION METHOD FOR FUNCTIONALIZING THE SURFACE OF MAGNETIC MICROPARTICLES WITH AN INORGANIC PHOSPHOROUS DENDRIMER

PRIORITY CLAIM

The present application is a non-provisional application claiming the benefit of U.S. Provisional Application No. 61/787,047, filed on Mar. 15, 2013 by Marie Archer, entitled "Large Scale Preparation Method for Functionalizing the Surface of Magnetic Microparticles with an Inorganic Phosphorous Dendrimer," the entire contents of which is incorporated herein by reference.

BACKGROUND OF THE INVENTION

1. Field of the Invention

The present invention relates to attaching a phosphorous dendrimer to magnetic microparticles.

2. Description of the Prior Art

The methods to fabricate magnetically responsive particles of sizes ranging from a few nanometers to several microns have been in continuous development for more than a decade. Magnetic microparticles of various sizes, compositions and different surface functionalities are commercially available for biological separations, immunoassays, and medical imaging. In general, these particles consist of a magnetizable core (for example iron oxide) coated with a polymer onto which a reactive functional group is linked. The reactive functional group can be an epoxy, amide, carboxyl, amino, hydroxyl, among others, and it is incorporated into the magnetic microparticles during the polymerization step. The presence of these reactive functional groups allows covalent or non-covalent interaction with biological moieties such as cells, cell organelles, nucleic acids, proteins and antibodies that facilitate their separation from other organelles, organisms or substances contained in the same matrix. Since all these processes are carried out in aqueous phases, the commercially available functionalized magnetic microparticles are usually sold as a suspension in water based storage solution, which limits their use in water based reactions.

In many circumstances, such as for the specific capture of genomic nucleic acids, it is necessary to attach a particular type of linker on the magnetic microparticle before linking a capture moiety to obtain the desired performance. If the linker required is only soluble in solvents with poor water solubility, the availability of magnetic microparticles in water based solutions represents a problem for the functionalization. Furthermore, none of the commercial providers have any information pertinent to the use of the magnetic microparticles in organic solvents nor have they developed protocols for their use under these conditions.

Phosphorous dendrimers are highly branched molecules soluble in solvents such as chloroform, tetrahydrofuran, dichloromethane, and dioxane. These molecules possess many characteristics that can enhance and facilitate capture of genomic nucleic acids in a single step when used as linkers in magnetic microparticles and other materials. A method to covalently attach a phosphorous dendrimer onto magnetic microparticles with primary amine functionality ($NH_2$) was previously disclosed (US Patent Publication 2008/0293594, the entire contents of which are incorporated herein by reference). Since the magnetic microparticles are suspended in water and the phosphorous dendrimer is only soluble in dichloromethane, it was necessary to perform a solvent exchange from water to dichloromethane of magnetic microparticles. The solvent exchange was done using ethanol as a transition solvent. Previously, a single transition step was used and the functionalization was performed in a small scale (500 μg of bead aliquots). The method of the present invention optimizes this approach by incorporating additional transition steps to make it suitable for small or large scale functionalization and in a shorter period of time. Both approaches are schematically shown in FIG. 1.

The only known approach that has considered the use of a dendrimer on the surface of a magnetic microparticle is that of Pan et al. (Pan et al., "Dendrimer modified magnetite nanoparticles for protein immobilization," *Journal of Colloid and Interface Science*, 284, 1-6 (2005)). However, Pan uses a cascading polyamidoamine dendrimer (PAMAM) and not a phosphorous dendrimer. Additionally, the dendrimer was synthesized on the surface of the magnetic microparticle by a stepwise deposition process through which layers of two different materials were incorporated until the desired dendrimer generations was reached. The resulting surface is covered with amine functionalities that cannot withstand the conditions required in the single step subtraction of genomic targets.

BRIEF SUMMARY OF THE INVENTION

The aforementioned problems are overcome in the present invention which provides a method of attaching a phosphorous dendrimer onto magnetic microparticles by taking magnetic microparticles in a water-based solution, then performing a solvent exchange, then suspending the microparticles in a phosphorous dendrimer solution and shaking (e.g. for 22 hours at 90 rpm), then washing the microparticles with an organic solvent, and then washing the microparticles with a transition solvent. The solvent exchange is done by washing the microparticles with a first concentration of a transition solvent (e.g. 50%), then washing the microparticles with a second concentration of the transition solvent (e.g. 100%) where the second concentration is greater than the first concentration, then washing the microparticles with an organic solvent, then washing the microparticles with the transition solvent, then washing the microparticles with the organic solvent, and then suspending the microparticles in the transition solvent. The transition solvent may comprise ethanol. The organic solvent may comprise dichloromethane, chloroform, tetrahydrofuran, dioxane, or any combination thereof. The phosphorous dendrimer may comprise hexachlorocyclotriphosphazene. Also disclosed is the related phosphorous dendrimer made by this method.

The present invention is intended to provide a large scale preparation method to incorporate phosphorous dendrimer linkers onto commercially available magnetic microparticles. The methods presented herein will enable the fabrication of magnetic microparticles with a phosphorous linker on their surface for use as selective solid phase for applications such as, but not limited to, subtraction of human genomic targets. For those applications requiring larger amounts of the solid phase to be prepared in single batches, the incorporation of the phosphorous dendrimer linker can be performed at a large scale while reducing the volume of hazardous materials required.

Functionalization of magnetic microparticles with a phosphorus dendrimer is required for the selective capturing of nucleic acids in a single step. Since the phosphorous dendrimer is soluble only in solvents with poor water solubility (tetrahydrofuran, dichloromethane, dioxane) and the magnetic microparticles are available only as suspensions in water based solutions, it is necessary to perform a solvent exchange process to achieve full functionalization. The phosphorous dendrimer cannot be incorporated onto the magnetic microparticles during its synthesis, and therefore a separate process has to be performed on the commercially available microparticles. In general, the use of these microparticles is intended for separation of biological moieties existing in water based environments. For this reason, none of the commercially available products has been characterized or tested in the presence of organic solvents such as the ones required for dissolving phosphorous dendrimers (dichloromethane, chloroform, tetrahydrofuran, dioxane). The present invention provides a method to functionalize commercially available magnetic microparticles with a phosphorous dendrimer. The method disclosed herein can be used for large scale functionalization of magnetic microparticles in a reproducible manner with a minimum amount of hazardous materials.

An advantage of the present invention is the possibility to functionalize commercially available magnetic microparticles with a phosphorus dendrimer, in a large scale, with reduced amount of hazardous material and a shorter processing time. The functionalization of magnetic microparticles with phosphorous dendrimers is relevant for the fabrication of selective solid phases for capturing genomic targets in a single step. Since the surface of the magnetic microparticles prepared with the method of the present invention is reactive towards biological moieties bearing primary amines, this method could be useful for the large scale fabrication of magnetic microparticles for other applications such as protein immobilization, or any separation requiring a reaction with an aldehyde group.

These and other features and advantages of the invention, as well as the invention itself, will become better understood by reference to the following detailed description, appended claims, and accompanying drawings.

BRIEF DESCRIPTION OF THE DRAWINGS

FIG. 1 shows a schematic comparison between (a) a previously disclosed method and (b) the method of the present invention for functionalizing magnetic microparticles.

DETAILED DESCRIPTION OF THE INVENTION

Figure 2:
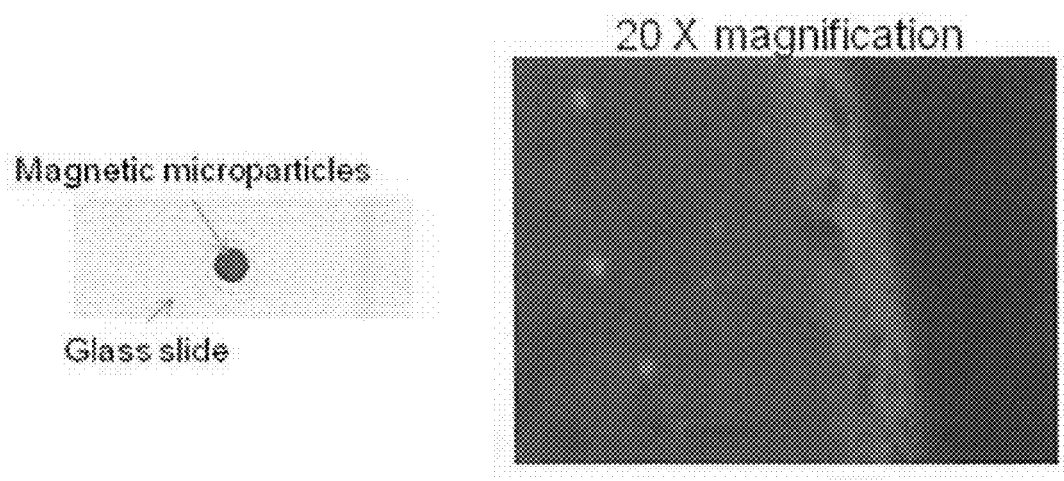
FIG. 2 is a fluorescence microscopy image of the magnetic microparticles functionalized with a 4.5 phosphorous dendrimer using the method of the present invention. A Cy3-amino oligonucleotide was used to corroborate the functionalization. The beads were dispersed on a glass slide and imaged at a 20× magnification.

The present invention relates in general to a method for the attachment of a phosphorous dendrimer onto magnetic microparticles. Particularly, this invention pertains to the attachment of phosphorous dendrimers, for example, but not limited to, phosphorous dendrimers with hexachlorocyclotriphosphazene core, onto magnetic microparticles with a primary amine to produce a solid phase suitable for the capture of genomic nucleic acids in a single step. Yet even more particularly, the invention concerns specific procedures to perform such attachment in the presence of a low water solubility organic solvent, for example, but not limited to, dichloromethane, by performing a solvent exchange using various concentrations of ethanol as a transition solvent.

Example

Method for Large Scale Functionalization of Magnetic Microparticles with Primary Amine Functionality with a Phosphorous Dendrimer in Dichloromethane Magnetic microbeads (~1 μm) with a primary amine functionality ($NH_2$) were purchased from Chemicall (Berlin, Germany) and functionalized following the steps described in FIG. 1(b). An aliquot of 10 mg of beads was washed once with 200 μl of water after removing the supernatant. The solvent exchange was performed by washing the beads twice with 400 μl of 50% ethanol and 100% ethanol each. The beads were then washed three times with 1 ml of dichloromethane, once with 1 ml of 100% ethanol and once with 1 ml of dichloromethane. The magnetic microparticles were then re-suspended in 1 ml of 100% ethanol and transferred to a fresh 2 ml polypropylene tube. The dendrimer immobilization was performed by adding 1.5 ml of a 2% (w/v) solution of generation 4.5 phosphorus dendrimer in dichloromethane, placed horizontally in an orbital shaker, and incubated for 22 hours at 90 rpms. After the immobilization period, the beads were washed 5 times with 1 ml of dichloromethane, three times with 1 ml of 100% ethanol, aliquoted in 200 μg into 1.5 ml polypropylene tubes, and dried in a heat block at 55° C. for 15 minutes after removing the remnant ethanol. To corroborate the immobilization of the dendrimer, a Cy3-amino labeled oligonucleotide was covalently attached to the beads. For this purpose, the prepared magnetic microparticles were re-suspended in 500 μl 0.3 M sodium phosphate buffer and incubated for 4 hours. The magnetic microparticles were re-suspended in 1 ml of fresh 0.3 M sodium phosphate buffer and incubated overnight at room temperature, and then transferred to a fresh 1.5 ml polypropylene tube. 150 μl of a solution of Cy3-amino labeled oligonucleotide at 30 ng/μl in 0.3 M sodium phosphate buffer was added to the beads and incubated in the dark for 4 hours with intermittent re-suspension. The magnetic microparticles were then blocked and washed according to the methods described in Archer et al., "Magnetic bead-based solid phase for selective extraction of genomic DNA," *Anal. Biochem.*, 355, 285-97 (2006) and Archer et al., "Development and Characterization of a Solid Phase for Single-Step Enrichment of Pathogenic Targets," *The Open Analytical Chemistry Journal*, 2, 47-54 (2008), the entire contents of each are incorporated herein by reference. For the fluorescence imaging, 5 μl of the magnetic microparticles were deposited on a clean glass slide and allowed to dry in the dark (FIG. 2). UV-spectroscopy measurement on the unbound oligonucleotide indicated an immobilization efficiency of 50%.

These results demonstrate the successful immobilization of the dendrimer on the magnetic microparticles. The amino modification of the oligonucleotide will react only with the aldehyde groups of the dendrimer, while the Cy3 modification produces the fluorescence signal. As a control experiment, magnetic microparticles not functionalized with the dendrimer were also imaged and did not exhibit fluorescence.

The above descriptions are those of the preferred embodiments of the invention. Various modifications and variations are possible in light of the above teachings without departing from the spirit and broader aspects of the invention. It is therefore to be understood that the claimed invention may be practiced otherwise than as specifically described. Any references to claim elements in the singular, for example, using the articles "a," "an," "the," or "said," is not to be construed as limiting the element to the singular.

What is claimed as new and desired to be protected by Letters Patent of the United States is:

1. A method to attach a phosphorous dendrimer onto magnetic microparticles, comprising:
    obtaining magnetic microparticles in a water-based solution and washing the microparticles with water; then performing a solvent exchange by washing the microparticles at least two times with a first concentration of a transition solvent, wherein the first concentration of transition solvent is 50%; then washing the microparticles at least two times with a second concentration of the transition solvent, wherein the second concentration is greater than the first concentration, and wherein the second concentration is 100%; then washing the microparticles at least three times with an organic solvent; then washing the microparticles with the transition solvent; then washing the microparticles with the organic solvent; and then suspending the microparticles in the transition solvent; then suspending the microparticles in a phosphorous dendrimer solution and shaking; then washing the microparticles at least five times with the organic solvent; and then washing the microparticles with the transition solvent.

2. The method of claim 1, wherein the microparticles comprise a primary amine functionality.

3. The method of claim 1, wherein the transition solvent comprises ethanol.

4. The method of claim 1, wherein the organic solvent comprises dichloromethane, chloroform, tetrahydrofuran, dioxane, or any combination thereof.

5. The method of claim 1, wherein the microparticles are 10 mg beads.

6. A method to attach a phosphorous dendrimer onto magnetic microparticles, comprising:

obtaining magnetic microparticles in a water-based solution and washing the microparticles with water; then performing a solvent exchange by washing the microparticles at least two times with a first concentration of a transition solvent; then washing the microparticles at least two times with a second concentration of the transition solvent wherein the second concentration is greater than the first concentration; then washing the microparticles at least three times with an organic solvent; then washing the microparticles with the transition solvent; then washing the microparticles with the organic solvent; and then suspending the microparticles in the transition solvent; then suspending the microparticles in a phosphorous dendrimer solution and shaking, wherein the shaking is for at least 22 hours at 90 rpm: then washing the microparticles at least five times with the organic solvent; and then washing the microparticles with the transition solvent.

7. A method to attach a phosphorous dendrimer onto magnetic microparticles, comprising:

obtaining magnetic microparticles in a water-based solution and washing the microparticles with water; then performing a solvent exchange by washing the microparticles at least two times with a first concentration of a transition solvent; then washing the microparticles at least two times with a second concentration of the transition solvent wherein the second concentration is greater than the first concentration; then washing the microparticles at least three times with an organic solvent; then washing the microparticles with the transition solvent; then washing the microparticles with the organic solvent; and then suspending the microparticles in the transition solvent; then suspending the microparticles in a phosphorous dendrimer solution and shaking; then washing the microparticles at least five times with the organic solvent; and then washing the microparticles with the transition solvent;

wherein the phosphorous dendrimer comprises hexachlorocyclotriphosphazene.

8. A phosphorous dendrimer attached to magnetic microparticles, made by the method comprising:

obtaining magnetic microparticles in a water-based solution and washing the microparticles with water; then performing a solvent exchange by washing the microparticles at least two times with a first concentration of a transition solvent, wherein the first concentration of transition solvent is 50%; then washing the microparticles at least two times with a second concentration of the transition solvent, wherein the second concentration is greater than the first concentration, and wherein the second concentration is 100%; then washing the microparticles at least three times with an organic solvent; then washing the microparticles with the transition solvent; then washing the microparticles with the organic solvent; and then suspending the microparticles in the transition solvent; then suspending the microparticles in a phosphorous dendrimer solution and shaking; then washing the microparticles at least five times with the organic solvent; and then washing the microparticles with the transition solvent.

9. The phosphorous dendrimer of claim 8, wherein the microparticles comprise a primary amine functionality.

10. The phosphorous dendrimer of claim 8, wherein the transition solvent comprises ethanol.

11. The phosphorous dendrimer of claim 8, wherein the organic solvent comprises dichloromethane, chloroform, tetrahydrofuran, dioxane, or any combination thereof.

12. The phosphorous dendrimer of claim 8, wherein the shaking is for at least 22 hours at 90 rpm.

13. The phosphorous dendrimer of claim 8, wherein the microparticles are 10 mg beads.

14. The phosphorous dendrimer of claim 8, wherein the phosphorous dendrimer comprises hexachlorocyclotriphosphazene.

15. The method of claim 6, wherein the microparticles comprise a primary amine functionality.

16. The method of claim 6, wherein the transition solvent comprises ethanol.

17. The method of claim 6, wherein the organic solvent comprises dichloromethane, chloroform, tetrahydrofuran, dioxane, or any combination thereof.

18. The method of claim 7, wherein the microparticles comprise a primary amine functionality.

19. The method of claim 7, wherein the transition solvent comprises ethanol.

20. The method of claim 7, wherein the organic solvent comprises dichloromethane, chloroform, tetrahydrofuran, dioxane, or any combination thereof.

\* \* \* \* \*